US00PP08385P

United States Patent [19]

Akerboom

[11] Patent Number: Plant 8,385

[45] Date of Patent: Sep. 21, 1993

[54] ASTER PLANT NAMED PINK SKIPPER

[76] Inventor: Petrus J. F. Akerboom, Paradijsweg 61, 2461 TL, Ter Aar, Netherlands

[21] Appl. No.: 895,728

[22] Filed: Jun. 9, 1992

[51] Int. Cl.[5] ..... A01H 5/00
[52] U.S. Cl. ..... Plt./68.1
[58] Field of Search ..... Plt./68.1

*Primary Examiner*—James R. Feyrer
*Attorney, Agent, or Firm*—Foley & Lardner

[57] ABSTRACT

A distinct cultivar of Aster plant named 'Pink Skipper', characterized by its cupped capitulum form, daisy capitulum type, purple ray floret color, capitulum diameter of 30 to 35 mm, strong well branched flower stems, and by its numerous flowers borne on short pedicels.

1 Drawing Sheet

The present invention comprises a new and distinct cultivar of Aster L. hereinafter referred to by the cultivar name 'Pink Skipper'.

'Pink Skipper' is a product of a planned breeding program which had the objective of creating new perennial Aster cultivars for year-round commercial production having well branched flower stems, large flower (capitulum) size, good flower (capitulum) form and shape, and having superior vase-life lasting quality of the cut flowers. Such traits in combination were not present or needed improvement in previously available commercial cultivars.

'Pink Skipper' was originated from a hybridization made by the inventor P. Akerboom in a controlled breeding program in Ter Aar, The Netherlands, in 1987. The female parent of 'Pink Skipper' was an unnamed *Aster pilosus* seedling. The male parent was an unnamed *Aster novi-belgii* seedling.

'Pink Skipper' was discovered and selected as one flowering plant within the progeny of the stated parentage by the inventor P. Akerboom on Sep. 10, 1987 in a controlled environment in Ter Aar and identified as seedling No. 87.M.K.B.D.R.2.G.

The first act of asexual reproduction of 'Pink Skipper' was accomplished when vegetative cuttings were taken from the initial selection in November 1987 in a controlled environment in Ter Aar by a technician working under formulations established and supervised by P. Akerboom.

Horticultural examination of selected units initiated in 1988 and 1989 has demonstrated that the unique combination of characteristics as herein disclosed for 'Pink Skipper' are firmly fixed and are retained through successive generations of asexual reproduction.

'Pink Skipper' has not been observed under all possible environmental conditions. The phenotype may vary significantly under different environmental conditions of temperature, light intensity and daylength, without, however, any variance in the genotype.

The following observations, measurements and comparisons describe plants grown in Ter Aar, The Netherlands, under greenhouse conditions which approximate those generally used in commercial greenhouse practice in this country. The following traits have been repeatedly observed and are determined to be basic characteristics of 'Pink Skipper', which, in combination, distinguish this Aster as a new and distinct cultivar:

1. Cupped capitulum form.

2. Daisy capitulum type.
3. Purple ray floret color.
4. Diameter across face of capitulum of 30 to 35 mm at maturity.
5. Strong, well branched flower stems.
6. Many capitula per synflorescence, borne on short pedicels.

The accompanying color photographic drawings show typical synflorescence of 'Pink Skipper', with the colors being as nearly true as possible with illustrations of this type.

The top photograph is a perspective view of 'Pink Skipper' grown as a single stem cut spray Aster.

The bottom photograph shows several flowers of 'Pink Skipper', with the ray floret color illustrated being more purple than the true color.

Of the commercial cultivars known to the inventor, the most similar to 'Pink Skipper' is the variety 'Rose Butterfly', disclosed in U.S. Plant Pat. No. 7,400. Reference is made to attached Chart A, which compares certain characteristics of 'Pink Skipper' to the same characteristics of 'Rose Butterfly'.

In comparison to 'Rose Butterfly', 'Pink Skipper' has more vigorous growth, thicker and courser flower stems, purple ray floret color ('Rose Butterfly' is pink), broader leaves, and ray florets which are lanceolate in shape and very narrow. Similar traits are capitulum form and type, spray formation, photoperiodic light reaction, and a generally similar number of ray florets.

In the following description color references are made to The Royal Horticultural Society Colour Chart. The color values were determined between 12:00 and 14:00 hours on Jun. 20, 1989 at Ter Aar, The Netherlands.

Classification:

*Botanical.*—*Aster pilosus* × *novi-belgii* cv 'Pink Skipper'.

*Commercial.*—Small daisy-like spray Aster perennial.

INFLORESCENCE

A. Capitulum:

*Form.*—Cupped.

*Type.*—Daisy.

*Diameter across face.*—30 to 35 mm.

*Arrangement.*—Raceme inflorescence.

B. Corolla of ray florets:

*Color (general tonality from a distance of three meters).*—Purple.

*Color (upper surface).*—Closest to 75A.

*Color (under surface).*—Closest to 75A.

*Shape of floret.*—Apex acute; short to medium, lanceolate, very narrow, straight.

*Size of floret.*—15-16 mm long×4-5 mm wide.

*Number of ray florets.*—25-30.

C. Corolla of disc florets:

*Color (mature).*—Closest to 1C/1D.

*Color (immature).*—Closest to 1C/1D.

*Diameter of disc.*—8-9 mm.

D. Reproductive organs:

*Androecium.*—Present on disc florets only; no pollen.

*Gynoecium.*—Present on both ray and disc florets.

PLANT

A. General appearance:

*Height.*—Tall; depends on light reaction; under continuous long days it can grow up to two meters tall; medium to dense branching.

B. Foliage:

*Color.*—RHS 147A to 136A.

*Shape.*—Linear.

*Size.*—Lower leaves, length 190-200 mm, relatively long; width 26-33 mm, broad. Upper leaves, length 110 mm; width 11 mm.

*Margin.*—Dentate on whole margin.

*Arrangement.*—Alternate, with angle recurvate.

CHART A
Comparison of 'Pink Skipper' and 'Rose Butterfly'

| Cultivar | PINK SKIPPER | ROSE BUTTERFLY |
|---|---|---|
| Ray floret color | Purple | Dark Pink |
| Capitulum form and type | Cupped daisy | Cupped daisy |
| Spray formation | Compound | Compound |
| Pedicels | 2-28 mm long | 5-15 mm long |
| Diameter across face of capitulum | 30-35 mm | 25-27 mm |
| Number of ray florets | 25-30 | 28-31 |

I claim:

1. A new and distinct cultivar of Aster named 'Pink Skipper', as illustrated and described.

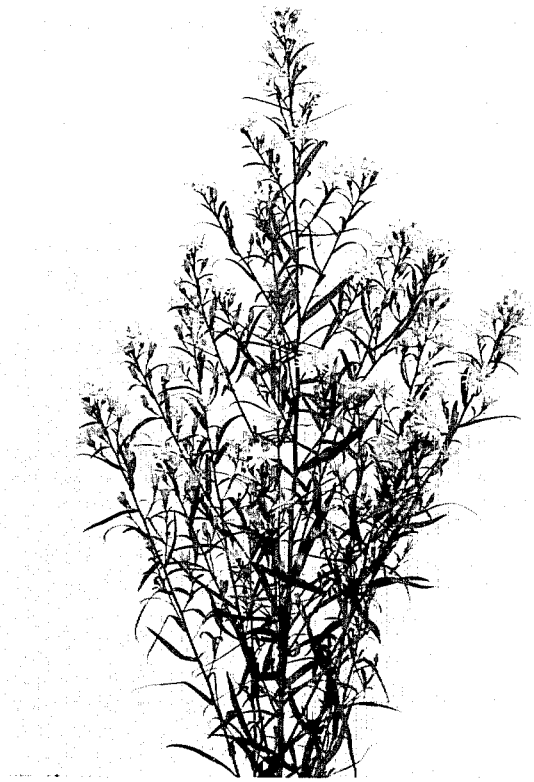
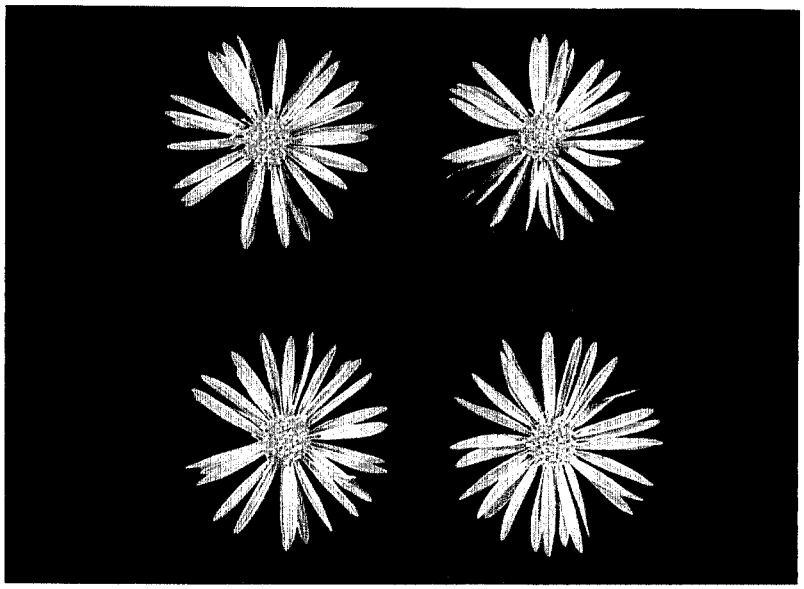

* * * * *